US00PP11014P

United States Patent [19]

Dorieux

[11] Patent Number: Plant 11,014

[45] Date of Patent: Jul. 27, 1999

[54] GRANDIFLORA ROSE PLANT NAMED 'DORIENT'

[75] Inventor: François Dorieux, Montagny, France

[73] Assignee: Bear Creek Gardens, Inc., Medford, Oreg.

[21] Appl. No.: 09/032,710

[22] Filed: Feb. 27, 1998

Related U.S. Application Data

[51] Int. Cl.[6] ..... A01H 5/00

[52] U.S. Cl. ..... Plt./130

[58] Field of Search ..... Plt./130, 138, 139, Plt./141, 149

[56] References Cited

U.S. PATENT DOCUMENTS

P.P. 8,568 2/1994 Warriner ..... Plt./130

*Primary Examiner*—Howard J. Locker

*Attorney, Agent, or Firm*—Klarquist Sparkman Campbell Leigh & Whinston, LLP

[57] ABSTRACT

Grandiflora rose plant having large purple flowers having strong fragrance; strong, vigorous habit of growth; glossy, disease resistant foliage; and free flowering with rapid rebloom.

1 Drawing Sheet

The present invention relates to a new and distinct variety of rose plant of the grandiflora class which was originated by me by crossing the variety 'DELdiore,' (unpatented), with the variety 'STEbigpu,' U.S. Plant Pat. No. 6,262.

The primary objective of this breeding was to produce a rose plant having large, purple colored flowers with strong fragrance; vigorous, upright growth; clean, disease resistant foliage, and the ability to produce many flowers. The objective was substantially achieved, along with other desirable improvements, as evidenced by the following unique combination of characteristics that are outstanding in the new variety and that distinguish it from its parents, as well as from all other varieties of which I am aware:

1. Very strong fragrance;
2. Purple colored flowers;
3. Strong, vigorous upright growth habit;
4. Glossy, disease resistant foliage;
5. Freely flowering with rapid rebloom.

Asexual reproduction of this new variety by budding, as performed at Wasco, Calif. and Montagny, France, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'DELdiore', (unpatented).

*Pollen parent.*—'STEbigpu,' U.S. Plant Pat. No. 6,262.

Classification:

*Botanical.*—Rosa hybrida.

*Commercial.*—Grandiflora.

FLOWER

Observations made from specimens grown in a garden environment at Montagny, France and at Somis, Calif. from Mar. 1996 to Nov. 1997.

Blooming habit: Recurrent.

Bud:

*Size.*—1½" long when the petals start to unfurl.

*Form.*—Long, pointed ovoid.

*Color.*—When sepals first divide, bud color is Greyed-Purple Group 184D. When half blown, the upper sides of the petals are Greyed-Purple Group 185B with some Greyed-Purple Group 185D on petal edges of the outermost petals, and the lower sides of the petals are Greyed-Purple Group 184D.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Funnel. Size: Medium (5/16"×5/16"). Surface: Smooth.

*Peduncle.*—Length: Medium (3" to 3½"). Surface: Smooth with a few glands. Color: Yellow-Green Group 146A and bronzy. Strength: Stiff, erect.

Bloom:

*Size.*—Large. Average open size is 4".

*Borne.*—Singly and several together in clusters of 3 to 7 blooms having a flat shape.

*Stems.*—Medium (14–18"), strong.

*Form.*—When first open: High centered. Permanence: All petals curl.

*Petalage.*—Number of petals under normal conditions: 25–30.

*Color.*—The upper sides of the petals are Greyed-Purple Group 185B with some fading on the outer edges of the outer petals to Greyed-Purple Group 185D. The inner one-third of all petals is Greyed-Purple Group 185D. The reverse sides of the petals are Greyed-Purple Group 184D. The base of each petal has a distinct (3/16"×3/16") Yellow-Orange Group 21C half moon at the point of attachment. The major color on the upper sides is Greyed-Purple Group 185B.

*Variegations.*—Occasional greenish-white streaks on the petals.

*Discoloration.*—At the end of the first day: No change. At the end of the third day: No change.

*Fragrance.*—Strong.

Petals:

*Texture.*—Thick.

*Shape.*—Round.

*Form.*—Tips slightly recurved.

*Arrangement.*—Imbricated. Petaloids in the center: Few, small.

*Persistence.*—Petals drop off cleanly before drying.

*Lastingness.*—On the plant: Long (7–8 days). As a cut flower: Long (9–10 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: White.

*Stigmas.*—Color: Greenish white.

Plant:

*Form.*—Bush.

*Growth.*—Very vigorous; upright; branching. At maturity, height is six feet, width is three and one-half feet.

Foliage: Number of leaflets on normal mid-stem leaves: Five or seven.

*Size.*—Large (7"×4½").

*Quantity.*—Abundant.

*Color.*—New foliage: Upper and lower sides: Greyed-Red Group 178A. Old foliage: Upper side: Green Group 139A. Lower side: Green Group 139C.

Leaflets:

*Shape.*—Pointed oval.

*Texture*—Upper side: Glossy, smooth.

*Edge.*—Serrated.

*Serration.*—Single, small.

*Petiole rachis.*—Color: Green Group 137A.

*Petiole underside.*—Smooth with occasional prickles.

*Stipules.*—Medium (7/16"), serrated, bearded.

*Disease resistance.*—Resistant to mildew and rust under normal growing conditions at Somis, Calif. and Montagny, France.

Wood:

*New wood.*—Color: Greyed-Red Group 178A, quickly turning green. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Medium, hooked downward.

*Color when young.*—Red Group 46A.

Small prickles:

*Quantity.*—On main stalks: Few. On laterals: Few.

*Color.*—Greyed-Orange Group 146C.

I claim:

1. A new and distinct variety of rose plant of the grandiflora class, as herein shown and described, characterized particularly by its large purple flowers having strong fragrance; strong, vigorous habit of growth; glossy, disease resistant foliage; and free flowering with rapid rebloom.

* * * * *

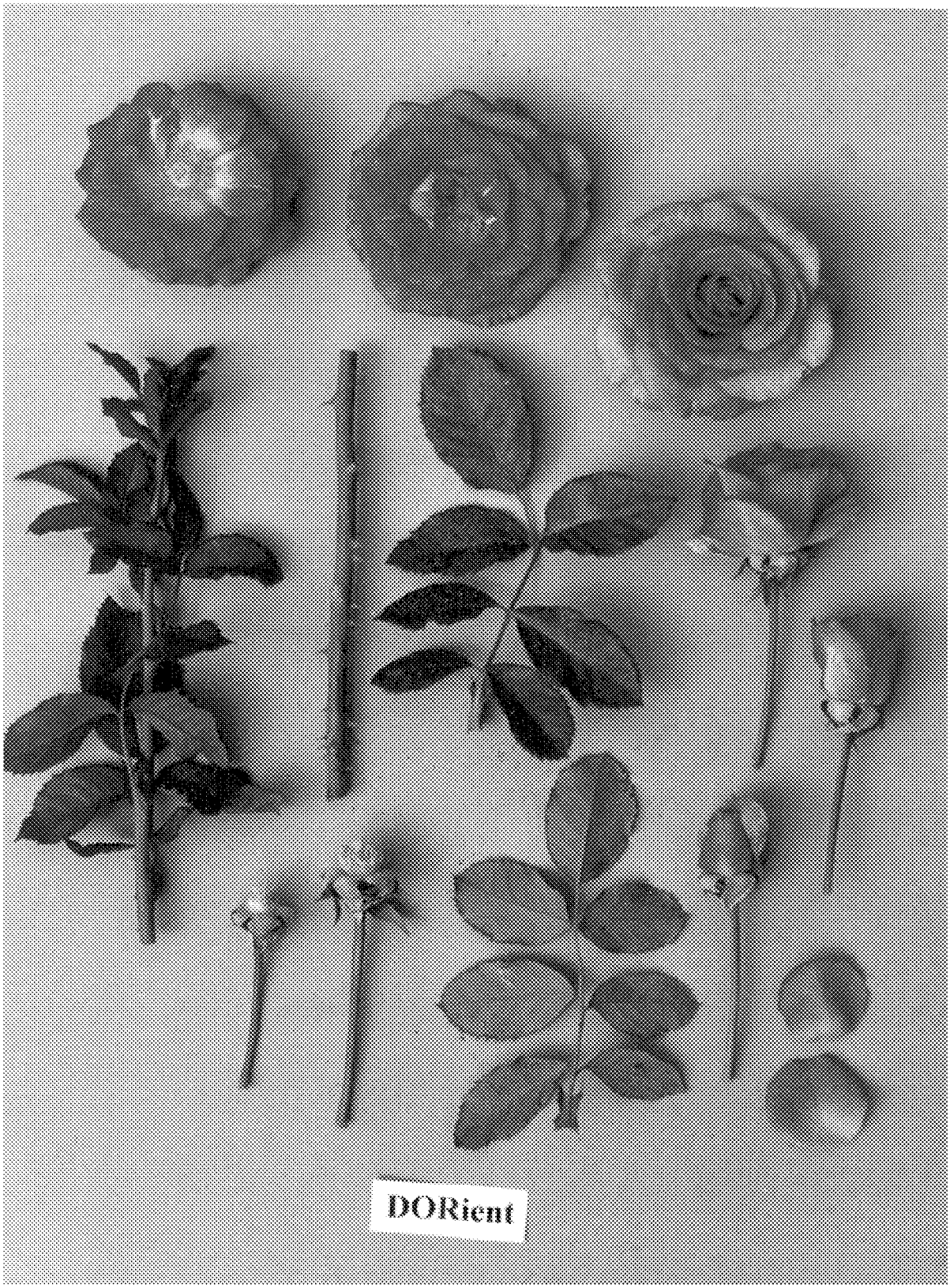
DORient